United States Patent [19]

Cole et al.

[11] Patent Number: 4,919,918

[45] Date of Patent: Apr. 24, 1990

[54] NON-ALCOHOLIC MOUTHWASH

[75] Inventors: B. Harrison Cole; Donald C. Kroeger; Mark E. Wilson, all of Houston, Tex.

[73] Assignee: Spectrum Consumer Products Co., Inc., Houston, Tex.

[21] Appl. No.: 167,504

[22] Filed: Mar. 14, 1988

[51] Int. Cl.⁵ .................. A61K 9/16; A61K 9/18; A61K 9/46

[52] U.S. Cl. ...................... 424/44; 424/49; 424/52; 424/54

[58] Field of Search .............. 424/44, 49, 52, 54

[56] References Cited

U.S. PATENT DOCUMENTS

| | | | |
|---|---|---|---|
| 3,518,343 | 6/1970 | Welsh et al. | 424/44 |
| 3,629,468 | 12/1971 | Andersen | 424/44 |
| 3,888,976 | 6/1975 | Mlkvy et al. | 424/44 |
| 3,943,949 | 3/1976 | Ashton et al. | 132/321 |
| 3,962,417 | 6/1976 | Howell | 424/44 |
| 4,033,365 | 7/1977 | Klepak et al. | 132/321 |
| 4,045,587 | 8/1977 | Katz et al. | |
| 4,127,645 | 11/1978 | Witzel et al. | |
| 4,248,895 | 2/1981 | Stroz et al. | |
| 4,259,355 | 3/1981 | Marmo et al. | |
| 4,291,045 | 9/1981 | Mackay et al. | |
| 4,374,122 | 2/1983 | Stroz et al. | |
| 4,419,346 | 12/1983 | Stroz et al. | |
| 4,457,921 | 7/1984 | Stroz et al. | |
| 4,508,713 | 4/1985 | Stroz et al. | |
| 4,515,769 | 5/1985 | Merritt et al. | |
| 4,568,560 | 2/1986 | Schobel | |
| 4,610,890 | 9/1986 | Miller et al. | |
| 4,627,972 | 12/1986 | Gioffre et al. | 424/44 |
| 4,657,758 | 4/1987 | Goldemberg et al. | |
| 4,666,708 | 5/1987 | Goldemberg et al. | |
| 4,689,235 | 8/1987 | Barnes et al. | |
| 4,695,463 | 9/1987 | Yang et al. | |
| 4,707,367 | 11/1987 | Miller et al. | |
| 4,752,481 | 6/1988 | Dokuzovic | |
| 4,753,805 | 6/1988 | Cherukuri et al. | |
| 4,803,082 | 2/1989 | Cherukuri et al. | |
| 4,816,265 | 3/1989 | Cherukuri et al. | |

Primary Examiner—Shep K. Rose
Attorney, Agent, or Firm—Cooper & Dunham

[57] ABSTRACT

A non-alcoholic effervescent compound for cleaning and disinfecting the mouth, teeth, gums and breath without necessity of alcohol as a solvent. Surface acting agents, or surfactants, are used to reduce surface tension of the compound in solution, facilitating dissolution of all additives including non-soluble oil-containing components. Surface acting agents also produce a foaming effect which loosens bacteria and food off and out from between teeth. The compound eliminates use of alcohol as a solvent, has increased cleaning action from both foaming and effervescence and produces a good-tasting, desirable mouthwash with appropriate flavor concentrations.

8 Claims, No Drawings

NON-ALCOHOLIC MOUTHWASH

BACKGROUND OF THE INVENTION

The present invention relates to a non-alcoholic compound in wet or dry form for cleaning the mouth, teeth, gums, and breath of individuals.

All individuals have varying minimum levels of bacteria found in their mouths. The source of the different types of bacteria are diverse and, for example, may range from eating, to atmospheric and environmental conditions, to a simple contact with unspecified articles or one's hands and fingers. While the general types of oral bacteria are not ever likely to be completely eliminated, effective control of harmful bacterial growth is desired for good oral hygiene.

The principal growth stimuli for harmful oral bacteria are residual food and food sugars coupled with the natural moisture and temperature conditions of the mouth. Under such conditions, these stimuli provide for explosive growth of harmful bacteria. These oral bacteria secrete acidic residues which further exacerbate and increase instances of poor health, dental caries, and periodontal disease.

Decaying food particles which become trapped between teeth or between teeth and gum areas are inconvenient or difficult to remove and contribute to higher levels of acidity and poor health, dental caries, and periodontal disease.

Compounds designed to clean the oral cavity and provide fresh breath are known. Generically, such compounds fall into two groupings; dentifrices and mouthwashes. Other compounds, generically described as breath mints or breath fresheners which may be delivered in gums, liquids, sprays, or small pill-like shapes, are not considered oral cavity cleaners.

Mouthwashes are over-the-counter solutions containing varying amounts of alcohol. Alcohol is used in mouthwash preparations as a solvent in which other additions such as anti-microbial agents, flavoring oils, color additives, fluoride, and astringents can be dissolved and caused to react in a water-base solution. For many such additive agents, alcohol is chemically and economically preferable as the universal solvent in conjunction with a water-base solution.

Utilizing alcohol in an oral hygiene preparation can have many detrimental side effects depending upon the user. Beyond presenting potential medical and health problems, its inclusion in oral hygiene products also presents potential social implications for some users. The medical implications of using alcohol in an oral hygiene preparation are validated by explicit warning labels on alcohol-based mouthwashes along with corrective actions to be taken if too much mouthwash is ingested.

Ingesting alcohol can have a range of little impact up to and including death, depending upon the individual. If the individual is a toddler or a person over age 60, there is a distinct difference in metabolic absorption capabilities as compared to persons between these age categories. Many widely-sold mouthwashes carry label warnings against use by individuals age six and under. It is generally known that as a person ages past 60 their general ability to metabolize alcohol gradually diminishes until digressing to approximately that of a six year old's metabolic absorption when reaching approximately 80 years old. Additionally, alcohol and its abuses in all forms is a recognized major social problem. Abuse of alcohol in all its forms is considered an illness, and in some schools of thought, is believed to be passed genetically. Contact with alcohol, which is readily absorbed through the mouth and into the blood, can trigger setbacks in recovering alcoholics.

Accidental poisonings by ingesting alcohol-based mouthwashes have occurred. The explicit prohibitions for children under the age of six along with corrective actions to be taken in such events attests to the potential danger of alcohol in oral hygiene products. Accidental ingestion of alcohol-based mouthwashes by diabetics may cause a dangerous insulin deficiency, as insulin is utilized by the body in digesting alcohol. Ingestion of alcohol by individuals under regular or periodic treatment with certain families of prescription drugs can render the drug either useless or, coupled with the alcohol, make the drug toxic to the individual user.

In addition to the above potential problems of using alcohol in an over-the-counter or prescriptive oral hygiene product, alcohol dehydrates the body cells and tissue, often killing such cells and tissue. Claims of presently available products' ability and performance of killing bacteria are outweighed by alcohol's effects on healthy cells and tissue. Alcohol is a non-specific, general antiseptic.

Beyond its presence as a bacterial antiseptic in the oral cavity and its use as a solvent for currently available additives, alcohol is also a product enhancement additive for commercially available solution compounds generically sold as mouthwashes. The solution containers are designed for multiple use, thus it is necessary to render the solution antiseptic, maintaining its clarity and preventing spoilage of the remaining solution.

Economically, alcohol is the preferred solvent for mouthwash additives. Nonetheless, an effective mouthwash compound which contains no alcohol is preferable.

Almost all liquid mouthwashes, whether alcohol-containing or not, are packaged as liquids whose principal volume and weight comprises water. They are packaged in clear plastic containers without protective outer packaging, and are subject to product tampering, such as by "hair hypodermic" needles which can inject contaminants or poisons without being noticed by the consumer. They are also significantly more expensive to transport from manufacturer to point-of-sale location because moving liquids is significantly more expensive on a per ounce dosage basis than a dry powder.

There is an important health advantage in the opportunity to use tamper-proof packaging. Further, transportation in a dry form, and packaging in single dosage, moisture-proof packets enclosed in a general external consumer package or box, makes it more difficult to contaminate the product without triggering an effervescent action of the dry, non-alcoholic mouthwash compound.

Dry and tablet form mouthwashes are known. U.S. Pat. Nos. 3,772,431 and 3,888,976 to Mikvy et. al. discloses a dry tablet compound which, upon dissolution, provides a solution with desensitizing action to the teeth, effervescent cleaning action, and gingival toning. Both patents merely disclose a basic mouthwash formulation, but do not address specific formulations or additive agents.

Effervescent mouthwash tablets are disclosed in U.S. Pat. Nos. 3,577,490, 3,629,468, and 3,518,343. Each of these patents concerns a method for the manufacture of effervescent tablets which may be used for cleaning solid surfaces, including the teeth and gum areas of the oral cavity. For example, U.S. Pat. Nos. 3,518,343 and 3,577,490 to Welsh et. al. address unsuccessful prior art effervescent tablets and the need for an effective tableting lubricant and water-soluble anti-microbial agent to improve manufacturing processes for water-soluble tablets containing anti-microbial agents. Welsh et. al. do not address specific formulations of such mouthwash compounds, but rather, disclose means to manufacture the tablets. U.S. Pat. No. 3,629,468 to Anderson also addresses inadequacies of prior methods of producing effervescent tablets and discloses a method of manufacture which eliminates heating and drying steps, increases storage life of the resulting product, and eliminates the need for inclusion, in the compounds, of inert fillers or buffers.

SUMMARY OF THE INVENTION

One object of the present invention is to provide a non-alcoholic mouthwash, supplied in liquid, granulated, solid, or tablet form, which effectively dissolves in water to produce a mouthwash with increased foaming action to scrub teeth, mouth and gums, and has concentrated taste and is colorless or has attractive coloring.

Another object of the present invention is to provide a non-alcoholic liquid mouthwash which retains the ability to display foaming characteristics long after addition of water.

The present invention is an improvement on the prior art, and discloses a good tasting, colorless or colored, non-alcoholic mouthwash enabling effective cleaning and disinfecting of the mouth, teeth, gums and breath, while avoiding the harmful effects of alcohol, which is used as a solvent in other mouthwashes. The present invention utilizes one or more of a group of surface acting agents, or surfactants, to act as a solvent, eliminating the need for alcohol and enabling the use of flavoring oils and coloration additives. Use of surfactants also enables the mouthwash of the present invention to be supplied wet or dry, without losing the effervescent-type cleaning action which occurs when water is added to the dry compound and which ceases several minutes thereafter. The foaming action of the surfactants is revitalized upon agitation in the mouth of a user.

DETAILED DESCRIPTION OF THE INVENTION

The present invention contemplates a non-alcoholic mouthwash compound, to be provided either pre-mixed with water, or in dry granular or tablet form. The dry mixture, when mixed with water, provides a colorless or colored liquid with intensified cleaning action and concentrated flavoring which looks and tastes like popular, liquid, alcohol-containing preparations and retains the ability to produce a foaming action, after effervescence has ceased, upon agitation in a user's mouth.

A family of surface acting agents, or surfactants, enables the present invention to provide an effective, good tasting, colorless or colored mouthwash which is also non-alcoholic. Surfactants, when dissolved, concentrate near the surface of the solution, forming a layer between the solution and other additives. The surfactants, including those additives that do not readily dissolve in water, render inclusion of alcohol unnecessary.

Surfactants which may be used for the purposes of the present invention are sodium laurylsulfate, sodium n-laurylsarcosinate, sodium alkylsulfoacetate, sulfocolaurate and sulfated monoglyceride. However, other surfactants known to those skilled in the art may be suitable for purposes of the present invention.

The invention involves the utilization of the family of surfactants to produce effective liquid and solid mouthwash. The surfactants act to disperse additives not easily dissolved in water, including volatile oils used to create concentrated flavoring, throughout the mouthwash compound, and to maintain dispersion. In addition to displaying solvent characteristics, some surfactants foam when agitated in solution, creating a cleaning effect which loosens bacteria off tooth and gum surfaces and pushes food particles out from between teeth. Other surfactants can be used to disperse and maintain foaming agents throughout the compound, which will also produce an added cleaning effect.

The mouthwash effervescent couple composition comprises at least one of each of a solid organic or inorganic acid and a solid base, such as any of the metal carbonate salts. The acid and base are both phamaceutically acceptable. When dissolved in an aqueous solution, the acid and base materials combine to produce carbon dioxide, and have an effervescent effect.

An adherent, such as sodium benzoate, may also be added to enable the mouthwash to have a long lasting effect by forming a film on the teeth and holding the active ingredients in contact with the teeth for a long period of time. An anti-microbial agent, such as cetyldimethyl benzylammonium chloride, can be usefully added to decrease incidence of bad breath and tooth decay by killing the bacteria that cause those conditions. An agent, such as pyrophosphate salts, can be added for effective tartar control and enhancement of oral hygiene. Further protection against tooth decay can be insured by the addition of effective quantities of fluoride to the basic formula. A coloration additive can also be used. Effective amounts of prescription compounds, such as chlorhexidine, which has proven effective in combating gingivitis and related periodontal disease, can also be added to the compound or solution and supplied under a physician's or dentist's care. Flavoring agents in the form of spray dried volatile oils can be added in such quantities to provide equal or greater taste as those present in alcohol-based mouthwashes.

Effective amounts of one or more of the abovementioned surfactants are added to the mouthwash composition to insure dissolution of all ingredients when mixed with water. The surfactants will act to disperse volatile oils uniformly throughout an aqueous solution when water is added, and to maintain dispersion.

The present invention can be mixed with water and bottled, or supplied dry in granular or tablet form. The dry mixture can be packaged in powdered form, for example, in unit dose, moisture proof packages. Traditional tablet lubricants may be added, and the mixture can be formed into tablets, through manufacturing techniques well known in the art. The tablets also may be packaged in individual moisture proof packages.

If desired, water can be added to the dry mixture and the resulting solution can be bottled as a wet mouthwash. The effervescent effect of the solid acid and solid base in solution will occur immediately upon addition of water to the dry mixture. When the liquid is agitated, the surfactants will create a foaming and cleaning action in the mouth of the ultimate user.

EXAMPLE

A presently preferred example of a formula for use in the present invention comprises the following elements or compounds:

58% effervescent couple
   3.5% sodium saccharin
   0.5% surfactant
   38% spray dried flavoring(s)

The above formulation uses more than 4.5 times the flavoring compounds than previously available mouthwashes. This significant increase in flavor concentration is permitted because of the use of sufficient quantities of surfactants. The present invention in dry form with its increased flavoring concentration can produce an equal or greater flavoring concentration as those found in liquid alcohol-based mouthwashes.

The example can be modified to include antimicrobials, chlorhexidine, pyrophosphate salts, fluorides and coloring agents. The sodium saccharin and/or spray dried flavoring percentages then will be incrementally reduced to compensate for the presence of one or more of the modifying components.

It should be appreciated that although the invention has been described with reference to the best modes presently known to the applicants, other modes and uses will be apparent to those skilled in the art upon review of the specification. Practice of such other modes and uses will not depart from the spirit and scope of the invention.

We claim:

1. A dry non-alcoholic mouthwash compound in tablet or in dry granular form adapted to be dissolved in water for cleaning and disinfecting an individual's mouth, teeth, gums and breath, comprising:
   (a) at least one solid, pharmaceutically acceptable acid and at least one solid, pharmaceutically acceptable base, which are adapted to react to produce carbon dioxide when dissolved in water causing effervescence;
   (b) about 38% by weight of at least one additive consisting of a volatile oil in spray-dried form for use as a flavoring agent;
   (c) an effective amount of one or more of the following surface acting agents selected from a group consisting essentially of sodium laurylsulfate, sodium n-laurylsarcosinate, sodium alkylsulfoacetate, sulfocolaurate, sulfated monoglyceride, and sodium monoglyceride, the surface acting agent acting as a solvent in water to reduce surface tension between the additive and the water, to disperse the flavoring agent, and to render the use of alcohol in the mouthwash unnecessary.

2. The compound according to claim 1 further comprising an effective amount of fluoride.

3. The compound according to claim 1, further comprising an effective amount of chlorhexidine.

4. The compound according to claim 1, further comprising an anti-microbial agent.

5. The compound according to claim 1, further comprising a tartar control agent.

6. The compound according to claim 1, wherein the additive is a colorizing agent.

7. A method for cleaning the oral cavity, comprising placing an aqueous solution of an effervescing couple, a quantity of about 38% by weight of spray dried volatile oil used as a flavoring agent, and one or more surface acting agents into the mouth and causing the surface acting agents to foam and disperse the flavoring agent by agitation of solution in the mouth.

8. A dry, non-alcoholic mouthwash compound adapted to be dissolved in water for cleaning and disinfecting an individual's mouth, gums and breath, comprising about 40%–70% of an effervescent acid-base couple, about 2%–10% of a sweetening ingredient, lens than about 1% of a surface acting agent; and about 38% by weight of a spray dried flavoring agent.

* * * * *